United States Patent [19]

Schurter et al.

[11] Patent Number: 5,002,604
[45] Date of Patent: Mar. 26, 1991

[54] 2-(4-(5-CHLORO-3-FLUOROPYRIDIN-2-YLOXY)-PHENOXY)-PROPIONIC ACID DERIVATIVES HAVING HERBICIDAL ACTIVITY

[75] Inventors: Rolf Schurter, Binningen; Hermann Rempfler, Ettingen, both of Switzerland

[73] Assignee: Ciba-Geigy Corporation, Ardsley, N.Y.

[21] Appl. No.: 285,372

[22] Filed: Dec. 16, 1988

Related U.S. Application Data

[63] Continuation of Ser. No. 62,937, Jun. 16, 1987, abandoned, which is a continuation of Ser. No. 858,729, May 2, 1986, abandoned, which is a continuation-in-part of Ser. No. 677,775, Dec. 3, 1984, abandoned, which is a continuation-in-part of Ser. No. 450,815, Dec. 20, 1982, Pat. No. 4,505,743.

[30] Foreign Application Priority Data

Dec. 31, 1981 [CH] Switzerland .................. 8372/81

[51] Int. Cl.$^5$ .................. C07D 213/64; A01N 43/40
[52] U.S. Cl. .................. 71/94; 546/301; 546/302
[58] Field of Search .................. 546/302; 71/94

[56] References Cited

U.S. PATENT DOCUMENTS

| | | |
|---|---|---|
| 4,083,714 | 4/1978 | Takahashi et al. .................. 71/94 |
| 4,092,151 | 5/1978 | Takahashi et al. .................. 71/94 |
| 4,105,435 | 8/1978 | Nishiyama et al. .................. 71/94 |
| 4,115,100 | 9/1978 | Schurter et al. .................. 71/94 |
| 4,133,675 | 1/1979 | Schurter et al. .................. 71/94 |
| 4,134,751 | 1/1979 | Nishiyama et al. .................. 71/94 |
| 4,140,520 | 2/1979 | Nishiyama et al. .................. 71/94 |
| 4,213,774 | 7/1980 | Schurter et al. .................. 71/94 |
| 4,213,775 | 7/1980 | Nagai et al. .................. 71/103 |
| 4,300,944 | 11/1981 | Böhner et al. .................. 71/94 |
| 4,317,913 | 3/1982 | Cartwright .................. 546/345 |
| 4,324,627 | 4/1982 | Cartwright .................. 204/158 |
| 4,414,391 | 11/1983 | Cartwright et al. .................. 546/302 |
| 4,565,568 | 1/1986 | Johnson et al. .................. 71/94 |

FOREIGN PATENT DOCUMENTS

| | | |
|---|---|---|
| 0000483 | 2/1977 | European Pat. Off. .................. 71/94 |
| 0008624 | 6/1979 | European Pat. Off. .................. 71/94 |
| 0050097 | 4/1982 | European Pat. Off. .................. 71/94 |
| 0097460 | 1/1984 | European Pat. Off. .................. 71/94 |
| 2419285 | 10/1979 | France .................. 546/302 |
| 2002368 | 2/1979 | United Kingdom .................. 546/302 |
| 2015995 | 9/1984 | United Kingdom .................. 71/94 |

OTHER PUBLICATIONS

Nishiyama et al., Chem. Abstracts, vol. 92, (9), Abst. No. 71056/2, Mar. 3, 1980.

Jacques et al., Enantiomers, Racemates and Resolutions, pp. 251–261, Wiley-Interscience Publishers, (1981).

March, Advanced Organic Chemistry, Second Edition, pp. 86, 87 and 104, 1977.

Primary Examiner—Alan L. Rotman
Attorney, Agent, or Firm—Edward McC. Roberts

[57] ABSTRACT

There are described novel 2-[4-(5-chloro-3-fluoropyridin-2-yloxy)-phenoxy]-propionic acids esters and -thioesters having a herbicidal action and an action reducing the growth of grasses, which compounds correspond to the formula I

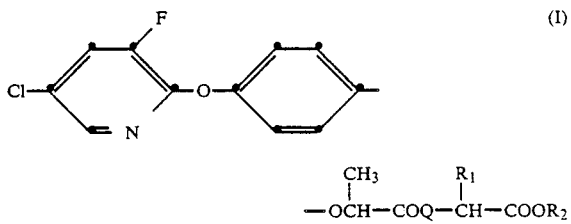

wherein Q is oxygen or sulfur,
$R_1$ is hydrogen or methyl
$R_2$ is hydrogen or $C_1$–$C_4$alkyl The salts and enantiomers of these compounds are also part of the invention.

These compounds are suitable for selectively controlling weeds in crops of cultivated plants, and for reducing the growth of grasses.

9 Claims, No Drawings

2-(4-(5-CHLORO-3-FLUOROPYRIDIN-2-YLOXY)-PHENOXY)-PROPIONIC ACID DERIVATIVES HAVING HERBICIDAL ACTIVITY

CROSS-REFERENCE TO RELATED APPLICATION

This application is a continuation of Ser. No. 07/062,937 filed 06/16/87 (abandoned), which is a continuation of Ser. No. 06/858,729 filed 05/02/86, (abandoned), which is a continuation-in-part of Ser. No. 06/677,775 filed 12/03/84, (abandoned), which is a continuation-in-part of Ser. No. 06/450,815, filed 12/20/82, now U.S. Pat. No. 4,505,743.

The present invention relates to novel 2-[4-(5-chloro-3-fluoropyridin-2-yloxy)-phenoxy]-propionic acid derivatives having herbicidal activity, to their production, to compositions containing these derivatives as active ingredients, and also to the use thereof as herbicides in general, and in particular for controlling weeds in crops of cultivated plants, such as cereals, rice, maize, soyabean and sugar beet.

The 2-[4-(5-chloro-3-fluoropyridin-2-yloxy)-phenoxy]-propionic acid derivatives correspond to the formula I

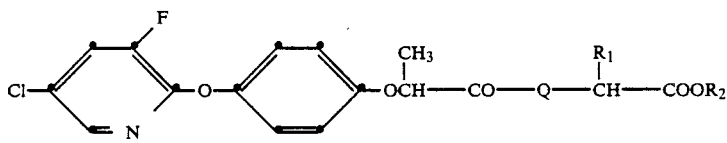

wherein
Q is oxygen or sulfur;
$R_1$ is hydrogen or methyl;
$R_2$ is hydrogen or $C_1$–$C_4$alkyl and to the salts and enantiomers of these compounds.

Especially effective are the following compounds and their (2R)-enantiomers:
2-[4-(5-chloro-3-fluoropyridin-2-yloxy)-phenoxy]-propionic acid methoxycarbonylmethyl ester,
2-[4-(5-chloro-3-fluoropyridin-2-yloxy)-phenoxy]-propionic acid methoxycarbonylmethylthioester,
2-[4-(5-chloro-3-fluoropyridin-2-yloxy)-phenoxy]-propionic acid ethoxycarbonylmethyl ester,
2-[4-(5-chloro-3-fluoropyridin-2-yloxy)-phenoxy]-propionic acid ethoxycarbonylmethylthio ester,
2-[4-(5-chloro-3-fluoropyridin-2-yloxy)-phenoxy]-propionic acid n-butoxycarbonylmethyl ester,
2-[4-(5-chloro-3-fluoropyridin-2-yloxy)-phenoxy]-propionic acid n-butoxycarbonylmethylthioester,
2-[4-(5-chloro-3-fluoropyridin-2-yloxy)-phenoxy]-propionic acid methoxycarbonyl-eth-1-yl ester,
2-[4-(5-chloro-3-fluoropyridin-2-yloxy)-phenoxy]-propionic acid methoxycarbonyl-eth-1-ylthio ester,
2-[4-(5-chloro-3-fluoropyridin-2-yloxy)-phenoxy]-propionic acid ethoxycarbonyl-eth-1-yl ester,
2-[4-(5-chloro-3-fluoropyridin-2-yloxy)-phenoxy]-propionic acid ethoxycarbonyl-eth-1-ylthio ester,
(2R)-2-[4-(5-chloro-3-fluoropyridin-2-yloxy)-phenoxy]-propionic acid methoxycarbonylmethyl ester,
(2R)-2-[4-(5-chloro-3-fluoropyridin-2-yloxy)-phenoxy]-propionic acid-methoxycarbonylmethylthio ester,
(2R)-2-[4-(5-chloro-3-fluoropyridin-2-yloxy)-phenoxy]-propionic acid methoxycarbonyl-eth-1-yl ester,
(2R)-2-[4-(5-chloro-3-fluoropyridin-2-yloxy)-phenoxy]-propionic acid ethoxycarbonylmethylthio ester.

The 2-[4-(5-chloro-3-fluoropyridin-2-yloxy)-phenoxy]-propionic acid esters according to the invention are characterised by a good action against mono- and some dicotyledonous weeds; they are above all effective in the post-emergence process against undesirable weeds and wild grasses occurring in cultivated crops, such as crops of cereals, maize, rice, soyabean and sugar beet. A particularly valuable aspect is that it is possible with the novel derivatives to combat wild grasses which are very difficult to control, for example Avena fatua, Avena sterilis, Alopecurus myosuroides, Lolium perenne, Phalaris sp. Bromus tectorum and various species of Setaria and Panicum. The action under field conditions is achieved even with small applied amounts of less than 1 kg per hectare, at which levels the cultivated crops are not harmed, or are harmed to only a negligible extent.

Halopyridyloxy-α-phenoxy-propionic acid derivatives have been described in numerous publications (cp. for example the German Offenlegungsschriften Nos. 2,546,251, 2,649,706, 2,714,622 and 2,715,284, and the European Publications Nos. 483 and 1473). In these publications, the 2-[4-(3-fluoro-5-halopyridin-2-yloxy)-phenoxy]-propionic acid derivatives according to the present invention have in part been taken into consideration and concomitantly included in the scope. Compounds of this type however have not been produced or tested. They are distinguished from the known halopyridyloxy-α-phenoxy-propionic acids by a better action.

The amounts applied can vary within wide limits, for example between 0.05 and 5 kg of active substance per hectare.

The novel compounds of the formula I can be produced by different methods which are mostly conventional.

One of these processes comprises reacting 5-chloro-2,3-difluoropyridine of the formula II

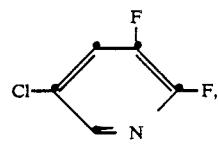

in an inert solvent or diluent and in the presence of the equimolar amount of a base, with a racemic or enantiomeric 4-hydroxyphenoxy-α-propionic acid ester of the formula III

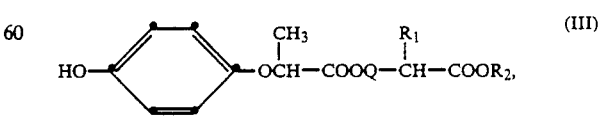

wherein Q, $R_1$ and $R_2$ have the meanings defined under the formula I.

A second process comprises reacting a 4-(5-chloro-3-fluoropyridin-2-yloxy)-phenol of the formula IV

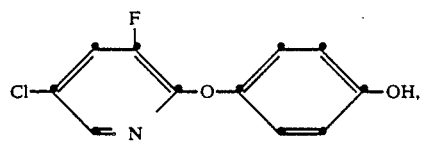

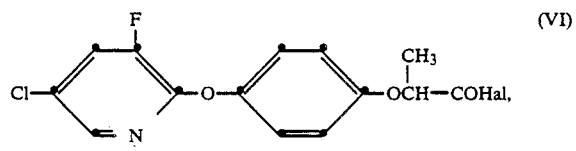

in an inert solvent or diluent and in the presence of the equimolar amount of a base, with a racemic or entantiomeric α-halopropionic acid ester of the formula V

wherein Hal is halogen, and Q, $R_1$ and $R_2$ have the meanings defined under the formula I.

A further process comprises reacting a racemic or enantiomeric 2-[4-(5-chloro-3-fluoropyridin-2-yloxy)-phenoxy]-propionic acid halide of the formula VI

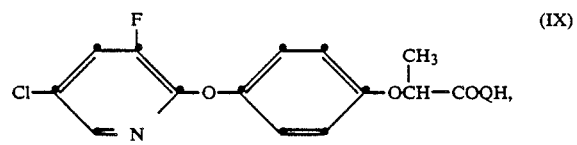

wherein Hal is halogen, in an inert solvent or diluent and in the presence of the equimolar amount of a base, with an alcohol or thiol of the formula VII $$HQ-\overset{R_1}{\underset{|}{CH}}-COOR_2, \quad (VII)$$

wherein Q, $R_1$ and $R_2$ have the meanings defined under the formula I.

In addition, the compounds of the formula I can be produced by reacting a racemic or enantiomeric 2-[4-(5-chloro-3-fluoropyridin-2-yloxy)-phenoxy]-propionic acid or -thiopropionic acid of the formula IX

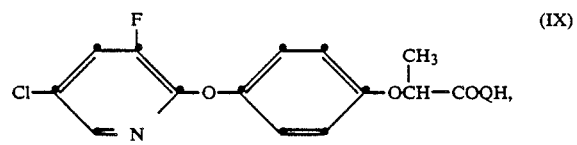

wherein Hal and Q have the meanings defined under the formula I, in an inert solvent or diluent and in the presence of the equimolar amount of a base, with a halide of the formula X $$\overset{R_1}{\underset{|}{Hal-CH}}-COOR_2 \quad (X)$$

wherein Hal is halogen, $R_1$ and $R_2$ have the meaning defined under the formula I.

Finally, a further process comprises converting a racematic or enantiomeric 2-[4-(5-chloro-3-fluoropyridin-2-yloxy)-phenoxy]-propionic acid ester of the formula XI

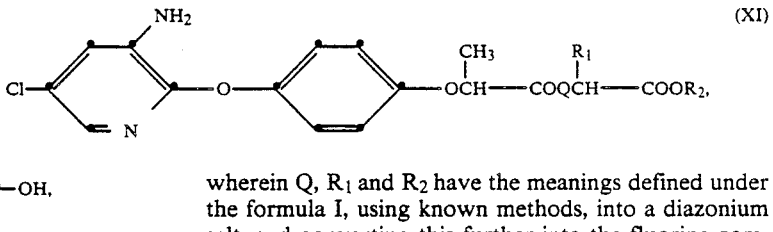

wherein Q, $R_1$ and $R_2$ have the meanings defined under the formula I, using known methods, into a diazonium salt, and converting this further into the fluorine compounds.

The (2R)-enantiomers of the compound of formula I are also prepared by reacting in an inert organic solvent in the presence of a base 4-(5-chloro-3-fluoropyridin-2-yloxy)-phenol of the formula IV

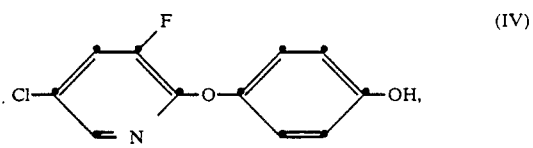

with (S)-lactic acid methylester-sulfonate of the formula XII $$R_3-SO_2O\overset{CH_3}{\underset{|}{CH}}-COOR, \quad (XII)$$

(2S)

wherein $R_3$ is a $C_1-C_6$ alkyl group which is straight-chain or branched, and which is unsubstituted or substituted by halogen, cyano, $C_1-C_4$ alkoxycarbonyl or is a phenyl group which is unsubstituted or substituted by $C_1-C_4$ alkyl, $C_1-C_4$ alkoxy, halogen, nitro, cyano, $C_1-C_4$alkoxycarbonyl and R is a $C_1-C_6$alkyl group, and converting the resulting (R)-2[4-(3-fluoro-5-halopyridin-2-yloxy)-phenoxy]-propionic acid ester obtained, by known procedures, to the corresponding (R)-2-[4-(3-fluoro-5-halopyridin-2-yloxy)-phenoxy]-propionic acid halide of the formula VI

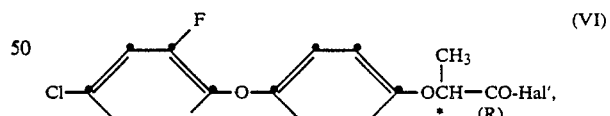

wherein Hal' is halogen and reacting this halide in an inert organic solvent in the presence of a base with an alcohol or thiol of the formula VII $$HQ-\overset{R_1}{\underset{|}{CH}}-COOR_2 \quad (VII)$$

wherein Q, $R_1$ and $R_2$ have the meanings given under formula I.

The starting material of formula II, 5-chloro-2,3-difluoropyridine may be prepared by fluorinating the corresponding 2,3,5-trichloropyridine in the presence of cesium fluoride. The products can be distilled off the reaction mixture and have to be purified by fractionate distillation. It is also possible to obtain 5-chloro-2,3-difluoropyridine starting from 2,5-dichloro-3-nitropyridine, which is reduced by means of hydrogen in the presence of e.g. Raney-nickel catalyst to 3-amino-2,5-dichloropyridine. This compound is then converted with sodium nitrite in the presence of hydrofluoric acid to 2,5-dichloro-3-fluoropyridine. This latter product can then be fluorinated in a good yield by means of potassium-fluoride to 2,3-difluoro-5-chloropyridine.

The starting material of formula IV 4-(5-chloro-3-fluoropyridin-2-yloxy)-phenol can be obtained by condensing in an inert organic solvent, in the presence of a base 5-chloro-2,3-difluoropyridine and hydroquinone.

The starting material of formula XI can be obtained e.g. by reducing the corresponding racemic or enantiomeric 2-[4-(5-chloro-3-nitropyridin-2-yloxy)-phenoxy]-propionic acid esters known e.g. from the German Offenlegungsschrift No. DE-A 2 732 846.

The remaining starting material are either known or can easily be prepared by conventional means.

A number of these reactions are advantageously carried out in an organic solvent or diluent inert to the reactants, for example an alcohol, ester, ether, ketone, dimethylformamide, dimethyl sulfoxide, acetonitrile, 1,1-dioxytetrahydrothiophene or an aromatic compound, such as toluene and xylene.

The reaction temperatures are between $-10°$ C. and $150°$ C., in practice however between room temperature and the boiling point of the solvent. Depending on the chosen starting material, the solvent and the temperature, the reaction time is between 1 hour up to about 1 day.

Where a halogen atom is detached in the reaction, the equimolar amount of an acid-binding agent should be used. Suitable as such is essentially any inorganic or organic base, for example NaOH, KOH, NaHCO$_3$, K$_2$CO$_3$ or K-tertbutylate, and amines, such as trimethylamine, triethylamine, pyridine, 4-dimethylaminopyridine, and so forth.

The novel active substances of the formula I are stable compounds which are soluble in customary organic solvents, such as alcohols, ethers, ketones, dimethylformamide, dimethyl sulfoxide, and the like. The compounds show favorable results in chronical toxicity studies to mammals.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ether and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acid or highly dispersed absorbent polymers. Suitable granulated adsorptive carriers are porous types, for example pumice, ground brick, sepiolite or bentonite; and suitable non-sorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{20}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarysulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkyarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulphates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1979, Sisely and Wood, "Encylopedia of Surface Active Agents", Chemical Publishing Co., Inc. New York, 1964.

These preparations contain as a rule 0.1 to 99%, particularly 0.1 to 95%, of active substance of the formula I, 1 to 99% of a solid or liquid additive, and 0 to 25%, especially 0.1 to 25%, of a tenside.

Whereas commercial products are preferably in the form of concentrated compositions, the compositions employed by the end-user are as a rule diluted.

The compositions can also contain further additives, such as stabilisers, antifoaming agents, viscosity regulators, binders and adhesives, and also fertilisers or other active ingredients for obtaining special effects.

The following Examples describe in detail the production of a 2-[4-(3-fluoro-5-chloropyridin-2-yloxy)-phenoxy]-propionic acid ester of the formula I according to the invention, and also compositions containing such esters as active ingredients. Further esters according to the invention which are obtained analogously are listed in the Table following Example 1. Percentages relate to weight.

EXAMPLE 1

Preparation of 2-[4-(5-chloro-3-fluoropyridin-2-yloxy)-phenoxy]-propionic acid ethoxycarbonylmethyl ester

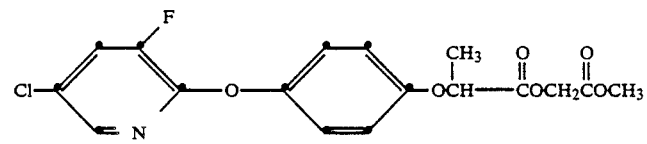

A mixture of 10.68 g (0.032 mol) of sodium 2-[4-(5-chloro-3-fluoropyridin-2-yloxy)-phenoxy]-propionate and 4.3 g (0.032 mol) bromacetic acid ethyl ester in 30 ml of dimethylformamide are heated for 1 hour at 80° C. The reaction mixture is then poured onto ice-water and extracted three times with ethylacetate. The extracts are washed with water, then with brine and dried over magnesium sulfate, filtered and concentrated by evaporation. The remaining oil is passed with petroleum ether/ether 1:1 over a short silicagel column. After the solvent has been evaporated off, there remains 10.2 g of a clear oil $n_D^{35}$ 1.5227.

The starting material, the sodium salt of 2-[4-(5-chloro-3-fluoropyridin-2-yloxy)-phenoxy]-propionate is obtained as follows:

(a) 3-amino-2,3-dichloropyridine

To a solution of 129.2 g (0.69 mol) of 2,5-dichloro-3-nitropyridine in 1300 ml of dioxane is added 26.0 g of Raney-nickel, that has previously been washed with ethanol. This mixture is then hydrogenated with hydrogen under normal pressure at 20°-35° C. After uptake of 20% of the theoretical amount of hydrogen, another 30 g of washed Raney-nickel catalyst are added. After hydrogenating for 22 hours, the catalyst is filtered off, the solvent is evaporated and the residue is crystallized from hexane/ethyl acetate. Thus, 84.9 g of 3-amino-2,5-dichloropyridine (78% of the theory) are obtained, which melts at 129°-132° C.

(b) 2,5-dichloro-3-fluoropyridine

To 450 ml (22.5 mol) of hydrogen fluoride in a stainless steel reaction vessel are added at a temperature of −5° to −1°, 163 g (1.0 mol) of 3-amino-2,5-dichloropyridine. Then there are added while stirring at the same temperature 82.8 g (1.2 mol) of sodium nitrite into the solution. The reaction mixture is stirred for 1.5 hours at −5° to −1°, then the temperature is slowly raised to +60° C. After the evolution of gas has ceased, the hydrogen fluoride is distilled off and the residue is taken up in methylene chloride. Ice/water is then added thereto and the cold mixture is neutralized with concentrated ammonium hydroxide solution. The organic phase separated and the water phase is extracted three times with methylene chloride. The organic phases are washed with water, dried over magnesium sulfate, filtered through silicagel and evaporated. Thus, 141.5 g (85% of the theory) of 2,5-dichloro-3-fluoropyridine are obtained.

(c) 5-chloro-2,3-difluoropyridine

A suspension of 64.6 g (1.1 mol) of potassium fluoride and 11.25 g (0.075 mol) of cesium-fluoride in 240 ml of sulfolane (1,1-dioxo-tetrahydrothiophene) is heated to 140° C. By reducing the pressure 50 ml of sulfolane are distilled off. To the suspension a solution of 61.4 g (0.37 mol) of 2,5-dichloro-3-fluoropyridine in 20 ml of sulfolane is added. The reaction-mixture is then stirred for 35 hours at a temperature of 140°, cooled and poured into ice/water. The organic material is extracted with ether. The ethereal layer is washed with water dried over magnesium sulfate, filtered and evaporated to yield 48.7 g of a colourless oil (88% of the theory) which boils at 65°-66° at 133 mbar.

(d)
2-[4-(5-chloro-3-fluoropyridin-2-yloxy)-phenoxy]-propionic acid methyl ester To a stirred mixture of 21.6 g (0.11 mol) of 2-(4-hydroxyphenoxy)-propionic acid methyl ester, 15.2 g (0.11 mol) of potassium carbonate, 1.45 g (0.0055 mol) of 18-Crown-6 ether and 100 ml of acetonitrile is added dropwise a solution of 14.95 g (0.10 mol) of 5-chloro-2,3-difluoropyridine in 30 ml of acetonitrile and the mixture is heated at a temperature of 50° to 60° C. during 40 hours. The mixture is then poured into ice/water. The organic material is extracted with ethyl acetate, washed with a saturated salt solution, dried over magnesium sulfate, filtered and evaporated. The oily residue is purified by chromatography over a silica gel column with a hexane/ethyl acetate 3:1 solvent. After evaporation of the solvent one obtain 20.4 g of the above ester (63% of the theory) is obtained in crystalline form. The melting point is 63°–64° C.

(e)
2-[4-(5-chloro-3-fluoropyridin-2-yloxy)-phenoxy]-propionic acid sodium salt To a solution of 13.0 g (0.04 mol) 2-[4-(5-chloro-3-fluoropyridin-2-yloxy)]-propionic acid methyl ester in 65 ml of dioxane is added 42 ml of 1N sodium hydroxide. Then it is stirred for 2½ hours at a temperature of 35° C. The mixture is then concentrated to dryness at room temperature in a rotatory evaporator. The remaining salt 13.2 g is used without further purification.

According to this example, the following compounds are prepared:

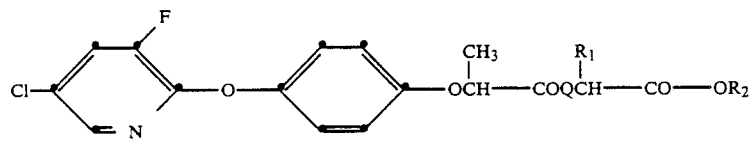

TABLE 1

| No. | $R_1$ | Q | $R_2$ | Physical data |
|---|---|---|---|---|
| 1.01 | $CH_3$ | O | $C_2H_5$ | $n_D^{35}$ 1.5227 |
| 1.02 | $CH_3$ | O | $CH_3$ | |
| 1.03 | $CH_3$ | S | $C_2H_5$ | |
| 1.04 | $CH_3$ | S | $CH_3$ | |
| 1.05 | H | O | $C_2H_5$ | |
| 1.06 | H | O | $CH_3$ | |
| 1.07 | H | S | $C_2H_5$ | |
| 1.08 | H | S | $CH_3$ | $n_D^{35}$ 1.5607 |
| 1.09 | H | O | $C_4H_9$-n | $n_D^{35}$ 1.5223 |
| 1.10 | H | S | $C_4H_9$-n | |

EXAMPLE 2

Preparation of the (R)-2-[4-(5-chloro-3-fluoropyridin-2-yloxy)-phenoxy]-propionic acid chloride

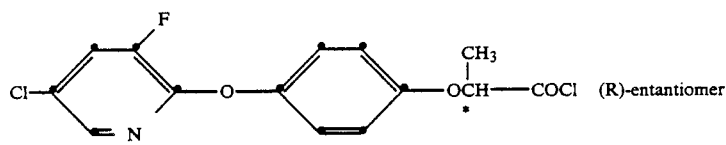

10.8 g (0.035 mol) of (R) (+)-2-[4-(5-chloro-3-fluoropyridin-2-yloxy)-phenoxy]-propionic acid are dissolved in 150 ml of toluene. Then 50 ml of toluene are distilled off in an oil-bath that has a temperature of 130°. The reaction mixture is then cooled down to 90° and 3.8 ml of thionyl chloride are added slowly thereto. The mixture is stirred for 16 hours at 90° and then evaporated under reduced pressure. The residue crystallizes and has a melting point of 47° to 48°.

This chloride is combined with esters of lactic and thiolactic acid to yield optically active esters of 4-(5-chloro-3-fluoro-pyridin-2-yloxy)-phenoxy]-propionic acid.

The enantiomers of Table 2 are prepared in this manner.

The (R) (+)-2-[4-(chloro-3-fluoropyridin-2-yloxy)-phenoxy]-propionic acid needed as starting material is obtained as follows:

(a) 4-(5-chloro-3-fluoropyridin-2-yloxy)-phenol

A mixture of 27.5 g (0.25 mol) of hydroquinone, 11.2 g (0.2 mol) of potassium hydroxide in 600 ml of dimethylsulfoxide is stirred at room temperature under a nitrogen atmosphere until everything is dissolved. A solution of 30 g (0.2 mol) of 5-chloro-2,3-difluoropyridine in 200 ml of dimethylsulfoxide is added dropwise thereto. The reaction mixture is then heated to 70° and stirred at that temperature for 4 hours. Then it is poured into ice/water and the mixture is acidified with hydrochloric acid, extracted with ethyl acetate, dried over magnesium sulfate, filtered and evaporated to dryness. The residue is taken up in a hexane/ethyl acetate 2:1 solvent and passed over a silicagel column for purification. After concentrating the eluate, the residue crystallizes to yield 33 g of white crystals, melting at 97°–98°.

(b) (R) (+)-2-[4-(5-chloro-3-fluoropyridin-2-yloxy)-phenoxy]-propionic acid methyl ester A solution of 24 g (0.1 mol) of 4-(5-chloro-3-fluoropyridin-2-yloxy)-phenol in 80 ml of dimethylsulfoxide is added dropwise to a stirred solution of 13.8 g (0.1 mol) of potassium carbonate in 50 ml of dimethylsulfoxide. When everything is added, the mixture is stirred for 2 hours at room temperature and then a solution of 25.8 g (0.1 mol) of (S)(−)-lactic acid-methylester tosylate is added dropwise over 30 minutes. The mixture is heated to 60° and stirred at that temperature for 20 hours, then poured onto ice/water and the organic material is extracted three times with ether. The ether-layer is washed with water and saturated salt solution, dried over magnesium sulfate, filtered and evaporated. The residue is passed for purification through a silicagel column with a hexane/ethyl acetate 3:1 solvent. After distillation of the solvent, 26 g of a clear oil of the above ester is obtained ($[\alpha]_D^{20} = +38.8° \pm 0.5°2\%$ in acetone).

(c) (R) (+)-2-[4-(5-chloro-3-fluoropyridin-2-yloxy)-phenoxy]-propionic acid

To a solution of 13.0 g (0.04 mol) of (R) (+)-2-[4-(5-chloro-3-fluoropyridin-2-yloxy)]-methyl ester in 65 ml of dioxane are added 42 ml of 1N sodium hydroxide and the mixture is stirred for 2½ hours at a temperature of 35°. Then it is poured onto an ice/water mixture and acidified with 22 ml of 2N hydrochloric acid. The organic material is extracted therefrom twice with ethyl acetate. The organic layers are washed with a saturated salt solution and dried over magnesium sulfate, filtered and concentrated. The residue is cristallized from ethyl acetate/hexane and yields 10.2 g (81.8% of the theory) of the above (2R) (+)-[4-(5-chloro-3-fluoropyridin-2-yloxy)-phenoxy]-propionic acid as white cristals, which melt at 95°-96° ($[\alpha]_D^{20} = +37.5° \pm 0.5°2\%$ in acetone).

EXAMPLE 3

Preparation of (2R,S) (+)-2-[4-(5-chloro-3-fluoropyridin-2-yl-oxy)-phenoxy]-propionic acid-ethoxycarbonyleth-1-yl ester

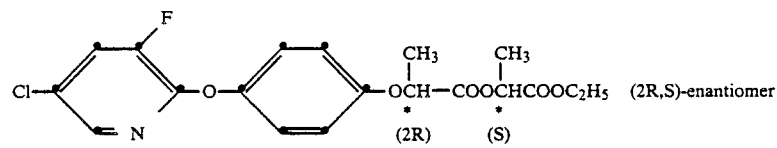

(2R,S)-enantiomer

A solution of 10.6 g (0.030 mol) of (R) (+)-2-[4-(5-chloro-3-fluoropyridin-2-yloxy)-phenoxy]-propionic acid chloride in 100 ml toluene is added slowly, while stirring into a solution of 4.9 ml (0.035 mol) of triethylamine and 2 ml (0.035 mol) of (S)-lactic acid ethyl ester in 40 ml of toluene, that is cooled in an ice-bath. When everything is added, the ice-bath is removed and the reaction mixture is stirred for 3 hours at room temperature. The reaction mixture is then poured into ice/water and the organic material is extracted twice with ethyl acetate. The ethyl acetate layer is washed with a saturated salt solution, dried over magnesium sulfate, filtered and evaporated. The residue is purified by chromatography over a silicagel column with a hexane/ethyl acetate solution. After evaporation of the solvent, there remains 8.9 g of the title product as a clear oil $n_D^{35}$ 1.5223, $[\alpha]_D^{20} = +20.4 \pm 0.4$ (acetone 0.02 g/l).

In analogy to Examples 2 and 3 the following 2R,S-enantiomers prepared:

EXAMPLE 4

Production of a formulation with liquid active ingredients of the formula I (%=percent by weight)

| Emulsion concentrates | (a) | (b) | (c) |
|---|---|---|---|
| 2-[4-(5-chloro-3-fluoropyridin-2-yloxy)-phenoxy]-propionic acid (ethoxycarbonyleth-1-yl) ester | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| Solutions | (a) | (b) | (c) | (d) |
|---|---|---|---|---|
| 2-[4-chloro-3-fluoropyridin-2-yloxy)-phenoxy-propionic acid methoxycarbonylthiomethyl ester | 80% | 10% | 5% | 95% |
| ethylene glycol-monomethyl ether | 20% | — | — | — |
| polyethylene glycol MG 400 | — | 70% | — | — |
| N-methyl-2-pyrrolidone | — | 20% | — | — |
| epoxidised coconut oil | — | — | 1% | 5% |
| ligroin (boiling limites 160–190° C.) | — | — | 94% | — |

The solutions are suitable for application in the form of very fine drops.

| Granulates | (a) | (b) |
|---|---|---|
| (R) (+)-2-[2-[4-(5-chloro-3-fluoropyridin-2-yloxy)-phenoxy]-propionic acid (ethoxycarbonyleth-1-yl) ester | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

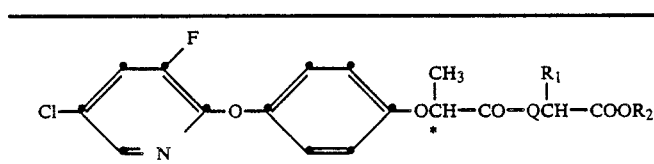

| No. | R₁ | Q | R₂ | phys. data |
|---|---|---|---|---|
| 2.01 | CH₃ | O | CH₃ | |
| 2.02 | H | S | CH₃ | $n_D^{35}$ 1.5623 $[\alpha]_D^{20}$ + 19.2 ± 0.5 (acetone 0.02 g/l) |
| 2.03 | CH₃ | O | C₂H₅ | $n_D^{35}$ .5223 $[\alpha]_D^{20}$ + 20.4 ± 0.4 (acetone 0.02 g/l) |

| Dusts | (a) | (b) |
|---|---|---|
| 2-[4-(5-chloro-3-fluoropyridin-2-yloxy)-phenoxy]-propionic acid ethoxycarbonylmethyl ester | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR SOLID ACTIVE INGREDIENTS OF THE FORMULA I (%=PERCENT BY WEIGHT)

| Wettable powders | (a) | (b) |
|---|---|---|
| 2-[4-(5-chloro-3-fluoropyridin-2-yloxy)-phenoxy]-propionic acid methoxycarbonyl-thiomethyl ester | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active ingredient is well mixed with the additives and the mixture is thoroughly ground in a suitable mill. Wettable powders which can be diluted with water to give suspensions of the required concentration are obtained.

| Emulsion concentrate | |
|---|---|
| (R) (+)-2-[4-[5-chloro-3-fluoropyridin-2-yl-oxy)-phenoxy]-propionic acid (methoxycar-bonylthioeth-1-yl) ester | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| Dusts | (a) | (b) |
|---|---|---|
| 2-[4-(5-chloro-3-fluoropyridin-2-yloxy)-phenoxy]-propionic acid (methoxycarbonyl-eth-1-yl) ester | 5% | 8% |
| talcum | 95% | — |
| kaolin | — | 92% |

Dusts ready for use are obtained by mixing the active substance with the carriers and grinding the mixture in a suitable mill.

| Extruder granulate | |
|---|---|
| 2-[4-(5-chloro-3-fluoropyridin-2-yloxy)-phenoxy]-propionic acid methoxycarbonyl-thiomethyl ester | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| Coated granulate | |
|---|---|
| 2-[4-(5-chloro-3-fluoropyridin-2-yloxy)-phenoxy]-propionic acid (ethoxycarbonyl-thioeth-1-yl) ester | 3% |
| polyethylene glycol (MG 200) | 3% |
| kaolin | 94% |

The finely ground active ingredient is evenly applied, in a mixer, to the kaolin moistened with polyethylene glycol. Dustfree coated granulates are obtained in this manner.

| Suspension concentrate | |
|---|---|
| (S) (−)-2-[4-(5-chloro-3-fluoropyridin-2-yloxy)-phenoxy]-propionic acid (ethoxy-carbonyleth-1-yl) ester | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

We claim:

1. A compound of the formula

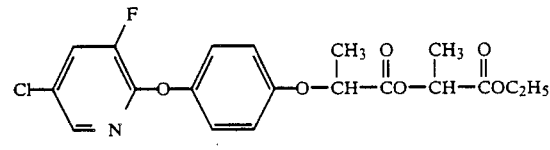

2. A herbicidal and plant growth regulating composition comprising an effective amount of a compound according to claim 1 in combination with an inert carrier.

3. The method of selectively controlling grasses in cereals comprising applying to the grasses or their locus of growth an effective amount of a compound according to claim 1.

4. A compound of the formula

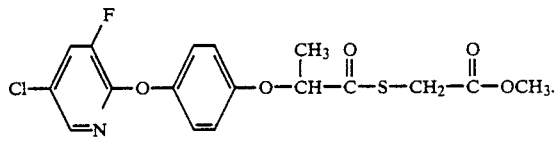

5. A herbicidal and plant growth regulating composition comprising an effective amount of a compound according to claim 4 in combination with an inert carrier.

6. The method of selectively controlling grasses in cereals comprising applying to the grasses or their locus of growth an effective amount of a compound according to claim 4.

7. The R(+)-enantiomer of the compound according to claim 4.

8. A herbicidal and plant growth regulating composition comprising an effective amount of a compound according to claim 7 in combination with an inert carrier.

9. The method of selectively controlling grasses in cereals comprising applying to the grasses or their locus of growth an effective amount of a compound according to claim 7.

* * * * *